United States Patent [19]
Dooley et al.

[11] Patent Number: 5,869,332
[45] Date of Patent: Feb. 9, 1999

[54] METASTATIC MELANOMA CELL LINES FROM MONODELPHIS DOMESTICA FOR USE IN ANTI-CANCER AGENT DISCOVERY

[75] Inventors: Thomas P. Dooley; Edward S. Robinson, both of San Antonio, Tex.

[73] Assignee: Southwest Foundation for Biomedical Research, San Antonio, Tex.

[21] Appl. No.: 253,376

[22] Filed: Jun. 3, 1994

[51] Int. Cl.$^6$ ...................................................... C12N 5/00
[52] U.S. Cl. ............................................ 435/325; 435/377
[58] Field of Search ................................ 435/240.2, 325, 435/377

[56] References Cited

PUBLICATIONS

Das Gupta, et al., Pediatr. Dermatol. 6:289–299 (1989).
Beattie, et al., Semin. Onco. 15:500–511 (1989).
Green, et al., Cancer Genet. Cytogenet. 61:71–92 (1992).
Ley, Photochem. Photobiol. 46:223–227 (1987).
Ley and Applegate, Models in Dermatology, pp. 265–275, ed. Maibach and Love (Basel: S. Karger, 1989).
Ley, et al., Photochem. Photobiol., 50:1–5 (1989).
Kusewit, et al., Vet. Pathol., 28:55–56 (1991).
Robinson, et al., Arch. Dermatol. Res. (1994, in press).
The Anticancer Drugs, 2nd ed., ed. Pratt et al. (N.Y.: Oxford Univ. Press, 1994).
Dooley, et al., Cancer Genet. Cytogent., 71:55–66 (1993).
Elder and Clark, Pigment Cell, 8:51–80 (1987).
Fidler, Nature New Biol. 245:148–149 (1973).
Donawho, et al., J. Immunother 12:187–193, (1992).
Bickers and Lowy, J. Invest. Dermatol. 92:121s–131s (1989).
Carrel and Rimoldt, Eur. J. Cancer 29A:1903–1907 (1993).
Rhodes et al., JAMA, 258:3146–3154 (1987).
Jimbow et al. Physiology, Biochemistry and Molecular Biology of the Skin, vol. II, ed. Goldsmith (N.Y.: Oxford Univ. Press, 1991).
NIH Consensus Development Panel on Early Melanoma, JAMA 268:1314–1319 (1992).
Elwood and Lee, Sem. Oncol., 2:149–154 (1975).
Dooley, Oncol. Res., 6:1–9 (1994).
Kruger and Pershing, Pharmacology of the Skin, ed. Mukhtar (London: CRC Press, 1992).
The Nude Mouse in Oncology Research, ed. Boven and Winograd (London: CRC Press, 1994).
Dooley, et al., Lab. Animals Sci., 13:48–57 (1993).
Bennett, et al., Int. J. Cancer, 39:414 (1987).
Dooley et al., Oncogene 3:531–536 (1988).
Wilson et al., Cancer Res. 49:711–716 (1989).
Fidler, et al., J. Natl. Cancer Inst. 67:947–956 (1981).
Yuspa and Dlugosz, Physiology, Biochemistry and Molecular Biology of the Skin, 2d ed., ed. Goldsmith (N.Y.: Oxford Univ. Press, 1991).
Iwamoto, et al., The EMBO J. 10:3167–3175 (1991).
Bradl., et al., Proc. Natl. Acad. Acad. Sci. 88:164–168 (1991).
Larue, et al. Oncogene 8:523–531 (1993).

*Primary Examiner*—Leon B. Lankford, Jr.
*Attorney, Agent, or Firm*—Cox & Smith Incorporated

[57] ABSTRACT

A cell line of metastatic, pigmented, malignant melanoma cells made by exposing a litter of *Monodelphis domestica* suckling young to an accumulated dose of ultraviolet radiation and then continuing the ultraviolet exposure after the young are weaned to induce malignant melanoma tumors and culturing the tumor cells from lymph nodes. This cell line can be used to test anti-cancer agents in vitro. Further this cell line can be injected into *Monodelphis domestica* suckling young so that tumors develop in the animals, and the anti-cancer agents can be tested in vivo.

4 Claims, 5 Drawing Sheets

METASTATIC MELANOMA CELL LINES FROM MONODELPHIS DOMESTICA FOR USE IN ANTI-CANCER AGENT DISCOVERY

FIELD OF THE INVENTION

The present invention relates to metastatic, pigmented, malignant melanoma cell lines from *Monodelphis domestica* for in vitro and in vivo experimental purposes and the methods and apparatus for producing such cell lines.

BACKGROUND OF THE INVENTION

The incidence of cutaneous malignant melanoma (CMM) is rapidly rising among Caucasians and is estimated to affect approximately one of every 100 Caucasian Americans within their lifetime. Melanoma results from the oncogenic transformation of the pigment-producing cells of the skin and hair, melanocytes. (Rhodes, et al., JAMA, 258:3146–3154 (1987); Jimbow, et al., *Physiology, Biochemistry and Molecular Biology of the Skin*, Vol. II, ed. Goldsmith, (N.Y.: Oxford Univ. Press, 1991); Elder and Clark, Pigment Cell, 8:51–80 (1987)). Although CMM is easily recognized clinically and treated surgically, this form of skin cancer causes about 6700 deaths each year in the USA, due to the propensity for melanoma to metastasize (NIH Consensus Development Panel on Early Melanoma, JAMA 268:1314–1319 (1992)), thus making it the most serious form of skin cancer. The risk factors for cutaneous melanoma include increased age, race, familial occurrence of this disease, ultraviolet radiation (UVR) exposure, dysplastic nevi, fair skin, among others. (Rhodes, et al. (1987); Jimbow, et al., (1991); Elder and Clark (1987); NIH, et al. (1992); Elwood and Lee., Sem. Oncol., 2:149–154 (1975)). Conventional chemotherapy strategies employing cytotoxic or anti-proliferative agents have not been highly successful for the treatment of metastatic melanoma to date. Therefore, oncologists are in need of more effective and safe therapies for the treatment of melanoma.

Several laboratory animal models have been developed to study various aspects of melanoma tumorigenesis, genetics, immunology and therapy (Dooley, Oncol. Res., 6:1–9 (1994)). Although no single animal model perfectly matches the genetic, biochemical, and pathological characteristics of human melanoma, each of the common models has some value in specific research areas for comparative studies relative to human melanoma. The established mammalian models, i.e. rodents (primarily mouse) and pigs (Sinclair swine) have some value in specific areas for comparative studies of human melanoma, but they do not provide a satisfactory match for the genetic, biochemical and pathological characteristics of the human disease.

Perhaps the most widely used mammalian model is mouse, although other rodent species have been used to a lesser degree. Mice derive their usefulness from the abundance of genetically-defined inbred strains. The minimal genetic heterogeneity within inbred strains permits cancer researchers to overcome many of the problems inherent in tumor transplantation studies, as both syngeneic and immunoincompetent strains (e.g., athymic nude mice) are available. (Kruger and Pershing, *Pharmacology of the Skin*, ed. Mukhtar (London: CRC Press, 1992); *The Nude Mouse in Oncology Research*, ed. Boven and Winograd (London: CRC Press, 1994); Dooley, et al., Lab. Animals Sci., 43:48–57 (1993)). Mice have been of great utility in the development of a variety of melanocytic cell lines exhibiting varying degrees of tumorigenicity and metastatic potential. (Kruger, et al, (1992); Bennett, et al., Int. J. Cancer, 39:414 (1987); Dooley, et al., Oncogene 3:531–536 (1988); Wilson, et al., Cancer Res. 49:711–716 (1989); Fidler, Nature New Biol. 245:148–149 (1973); Fidler, et al., J. Natl. Cancer Inst. 67:947–956 (1981)). Furthermore, immunoincompetent strains, such as nude and skid mice, are permissive for growth of melanoma cell lines from murine sources.

In some inbred mouse strains, treatment of shaved skin with a combination of chemical carcinogens (e.g., DMBA, croton oil, TPA, etc.) or a chemical carcinogen plus UVR produces melanocytic lesions. (Donawho, et al., J. Immunother, 12:187–193 (1992); Yuspa and Dlugosz, Physiology, Biochemistry and Molecular Biology of the Skin, 2d ed., ed. Goldsmith (N.Y.: Oxford Univ. Press, 1991); Bickers and Lowy, J. Invest. Dermatol. 92:121s–131s (1989)). However, treatment of murine skin by a single agent alone seldom or never produces any of these melanocytic lesions.

In the past few years, transgenic mouse models have been created that spontaneously develop melanomas. However, the tumors generally lack pigment. (Iwamoto, et al., The EMBO J. 10:3167–3175 (1991); Bradl., et al., Proc. Natl., Acad., Sci. 88:164–168 (1991); Larue, et al. Oncogene 8:523–531 (1993)). The transgenic melanoma models, utilizing the melanocyte-specific tyrosinase promoter fused to an activated oncogene, are showing significant promise for experimental studies of the cooperativity between known oncogenes and additional factors, such as UVR, tumor promoters, etc., but their potential utility in chemotherapeutic drug discovery efforts has not been examined.

A heritable form of congenital malignant melanoma is associated with Sinclair swine. This variety of pigs develops malignant melanomas in utero. The tumors exhibit rapid growth, invasion, and life-threatening metastases. (Dasgupta, et al., Pediatr. Dermatol. 6:289–299 (1989); Beattie, et al., Semin. Onco. 15:500–511 (1989); Green, et al., Cancer Genet. Cytogenet. 61:71–92 (1992)). Remarkably, some of these affected animals subsequently develop an immunological rejection of the tumors. In some instances, the anti-melanoma rejection process results in cutaneous vitiligo, presumably due to the ablation of normal skin melanocytes expressing antigenic determinants similar to the melanoma cells. This model is very promising both for the genetics of congenital melanoma induction and for the immunology of tumor rejection, but does not serve as an allogeneic grafting model.

With regard to experimental human melanoma studies, the availability of a large number of metastatic melanoma cell lines capable of growth in vitro has significantly advanced our understanding of melanoma biology. In addition, human metastatic cell lines have been grown by xenotransplantation in vivo in immunoincompetent nude mice, primarily for investigations of antineoplastic therapies. Human melanoma cell lines have also been of value in recent years for immunological studies, including the development of: (a) anti-melanoma antibodies directed against tumor-associated antigens (Carrel and Rimoldt, Eur. J. Cancer 29A:1903–1907 (1993)); (b) potential anti-tumor vaccines (Carrel, et al. (1993)); and (c) recently-conceived gene therapies. Human melanoma cell lines have also been used in oncogenesis studies.

The establishment of the laboratory opossum (*Monodelphis domestica*) as a useful melanoma model resulted from the dermatological and photobiological experiments of Dr. R. D. Ley and colleagues in Albuquerque, N. Mex. (Ley, Photochem. Photobiol. 46:223–227 (1987); Ley and Applegate, Models in Dermatology, pp. 265–275, ed. Maibach and Love (Basel: S. Karger, 1989)). One attractive aspect of the model is that, unique among the mammalian species so far examined, benign and malignant melanomas can be induced by chronic ultraviolet radiation exposure alone, without the concomitant requirement of application of chemical carcinogens. (Ley, et al., Photochem. Photobiol., 50:1–5 (1989); Kusewit, et al., Vet. Pathol., 28:55–56 (1991)). Pedigrees of a large Monodelphis colony maintained at the Southwest Foundation for Biomedical Research (SFBR) have been carefully documented since the first founders were imported in 1978. (VanOorschot, et al., Lab. Anim. Sci., 42:255–260 (1992)). Using the established sunlamp exposure protocol for exposing animals with suberythemal doses for up to 45 weeks, nevi were induced in 14% of those introduced to the protocol as adults. None of the nevi, however, progressed to metastatic melanoma. (VandeBerg, et al., Arch. Dermatol. Res. 286:12–17 (1994)). In a follow-up study, animals were introduced to the same protocol at the earlier weanling stage and two (2%) percent developed melanocytic nevi. A single animal developed malignant melanoma with presumptive metastasis to the spleen. (Robinson, et al., Arch. Dermatol. Res. 287:333–337 (1995)).

Some features of the established adult UVR exposure protocol impose limitations on its effective use. For example, it is time consuming, labor intensive, and therefore expensive. Most of the animals maintained on the protocol for up to one year are uninformative, and while the general state of health of exposed animals remains satisfactory, chronic exposure frequently leads to an undesirable side effect in the form of aggressive eye tumors. Furthermore, by the end of the protocol, animals are too old to mate, thus precluding their use in a breeding program.

The feature that most clearly distinguishes marsupials from other mammals is the immaturity of their young at birth. Neonate skin in Moiodelphis is thin, hairless, and not fully differentiated and is likely to absorb more ultraviolet radiation than adult skin. Monodelphis females, unlike the great majority of female marsupials do not possess a pouch so neonates are exposed on the mother's ventral surface. Thus, entire litters can be exposed to UVR and affected individuals can be used later for breeding. Furthermore, Monodelphis suckling young may serve as recipients for injection of tumor cells, due to underdeveloped immunosurveillance.

SUMMARY OF THE INVENTION

The purpose of this section is to summarize the principal aspects of the invention which are claimed.

It is a general object of the present invention to provide a malignant melanoma cell line which is useful for in vivo and in vitro experiments regarding the treatment of human melanoma.

One embodiment of the present invention is to provide a method of inducing malignant melanoma in *Monodelphis domestica* comprising the steps of: (a) exposing a litter of *Monodelphis domestica* animals, each attached to its mother's teat, to ultraviolet radiation in a series of approximately six to ten separate exposures, the series of exposures beginning at most four days postpartum and ending before each of the young becomes detached from its mother's teat; (b) shaving the animals of the litter exposed in step (a) at or soon after weaning or up to sixteen weeks post weaning to find externally visible dorsal skin melanocytic nevi; (c) exposing the shaved animals of step (b) to ultraviolet radiation at least three times per week for at most forty weeks; and (d) examining the young exposed in step (c) for melanoma.

It is another embodiment of the present invention to provide a cell line of metastatic, pigmented, malignant melanoma cells obtained from lymph nodes of *Monodelphis domestica*, which malignant melanoma cells are induced by exposing the suckling young of *Monodelphis domestica* to ultraviolet radiation, comprising the steps of: (a) euthanizing the animals that exhibit melanocytic nevi or melanoma; (b) examining lymph nodes from the animals euthanized in step (a) to find pigmented malignant melanoma cells; (c) biopsying lymph nodes from each of the animals that appear to have pigmented malignant melanoma cells after being examined in step (b); (d) mincing each of the biopsied lymph nodes from step (c); and (e) culturing each of the minced lymph nodes from step (d) in a culture medium. In a preferred embodiment of the present invention, the culturing step is conducted between 31° and 35° C.

Another embodiment of the present invention is to provide a Monodelphis having a cell line-induced, malignant melanoma growth and a method of inducing such in vitro melanoma growth in the Monodelphis comprising the step of injecting the Monodelphis with an amount of cells from the cell line.

Another embodiment of the present invention is to provide a method of in vivo testing potential anti-cancer agents in Monodelphis having a cell line-induced, malignant melanoma growth, comprising the steps of (a) injecting the Monodelphis having a cell-line induced, malignant melanoma growth with non-lethal amounts of an anti-cancer agent; and (b) determining the effect of the anti-cancer agent on the metastatic, pigmented, malignant melanoma growth.

Still another embodiment of the present invention is to provide a method of in vitro testing of potential anti-cancer agents on a cell line of metastatic, pigmented, malignant melanoma cells, comprising the steps of (a) adding an amount of an anti-cancer agent to a vessel containing an amount of the cell line; and (b) determining the effect of the anti-cancer agent on growth of the cell line.

Various other objects and advantages of the present invention will become apparent from the following figures and description of the invention.

BRIEF DESCRIPTION OF THE DRAWINGS

The file of this patent contains at least one drawing executed in color. Copies of this patent with color drawing(s) will be provided by the Patent and Trademark Office upon request and payment of the necessary fees.

DETAILED DESCRIPTION OF THE INVENTION

Figure 1:
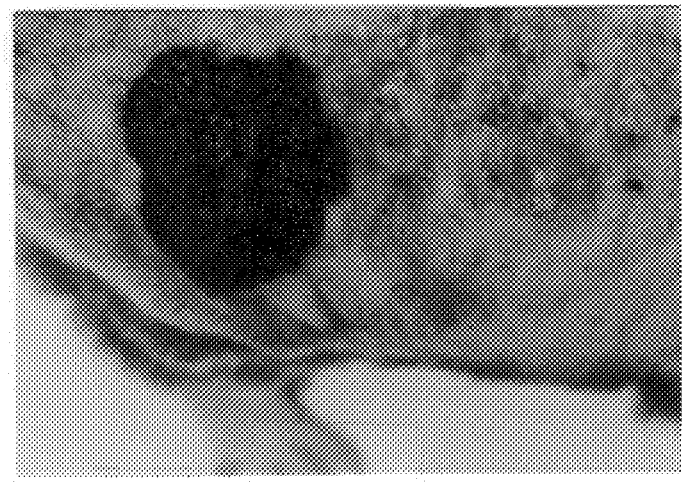
FIG. 1 is a malignant melanoma in dorsal skin of an adult Monodelphis, initiated by UVR exposures at the suckling stage.
Figure 2:
FIG. 2 is a darkened suprascapular lymph node of Monodelphis (arrow) containing pigmented melanoma cells.
Figure 3:
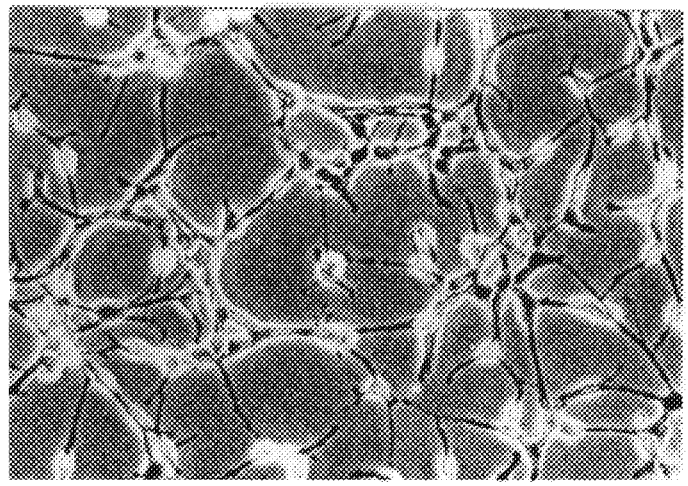
FIG. 3 is a cell line TD15L1 derived from a Monodelphis lymph node containing pigmented, dendritic melanoma cells.
Figure 4:
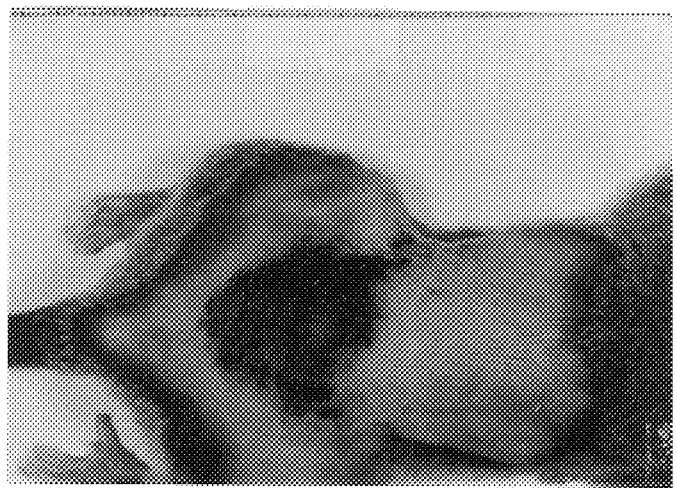
FIG. 4 is a malignant melanoma in dorsal skin of an adult Monodelphis, injected subcutaneously at the suckling stage with TD15L1 cells.
Figure 5:
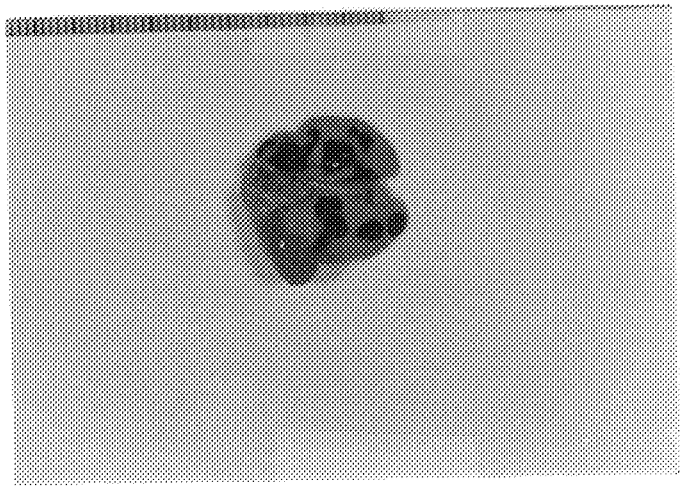
FIG. 5 is lung metastases in adult Monodelphis injected subcutaneously with TD 15L1 cells.

It is a general object of the present invention to provide a metastatic malignant melanoma cell line which is useful for in vivo and in vitro experiments with relevance to the development of novel means of treatment of human melanoma.

A variety of rodent and human metastatic melanoma cell lines have been previously developed for in vivo tumor studies, primarily involving immunoincompetent nude mice. However, these approaches lack two key features of the present invention: the recipient host mice are either totally immunoincompetent and thus are permissive for growth of tumor cells from a variety of species, or the mice are inbred immunocompetent host lines that are permissive only for syngeneic tumor cell growth (i.e., derived from only that particular mouse strain). The present invention overcomes these disadvantages, without the need for immunosuppressive agents in recipient hosts.

Metastic, pigmented malignant melanoma cell lines (e.g., derivatives of TD15L and TD18L) have been developed from Monodelphis lymph nodes. Cell line TD15L2 (ATCC No. CRL-11898), a cell line of pigmented, dendritic melanoma cells, was deposited in the American Type Culture Collection (ATCC), 12301 Parklawn Drive, Rockville, Md. 20852 on May 25, 1995. It has been shown that these new lines can be grown as primary and metastatic tumors in allografting experiments by injecting cells from these pigmented malignant melanoma cell lines into Moiodelphis suckling young. The tumor-bearing Monodelphis suckling young develop into fully immunocompetent hosts, albeit presumably not recognizing the previously-injected tumor cells in most instances. These animals do not require special quarantine or pathogen-free containment facilities, unlike nude mice.

Additional advantages of these cell lines (e.g., TD15L1 and TD15L2) include: the cell lines exhibit the propensity to metastasize (primarily to the lung) yielding pigmented lesions, permitting easy clinical assessment of tumor cell burden. The TD15L1 and TD15L2 (ATCC No. CRL-11898) melanoma lines have a specific cytogenetic marker to discriminate between tumor and host cells. Furthermore, use of the cell lines reduces the need for whole animal chronic UVR exposure to generate melanocytic lesions.

These metastatic melanoma cell lines are useful reagents for the discovery and development of novel anti-cancer therapies (*The Anticancer Drugs*, 2nd. ed., ed. Pratt et al. (N.Y.: Oxford Univ. Press, 1994)). Several types of experimental approaches can utilize these cell lines in vitro and in vivo, including conventional chemotherapies, immunomodulatory therapies, and gene therapies affecting either melanoma cells or lymphocytes are now possible. Examples of these therapies include: cytostatic agents, biological response modifiers, cytokine expressing agents, gene therapy vector agents, immunotoxin agents, antiproliferative agents, anti-metastasis agents, and angiostatic agents. The use of these melanoma cell lines in allografting with partially inbred Monodelphis (i.e., possessing inbreeding coefficients as low as 0.050) mimics the outbred (i.e., individuals are genetically dissimilar) and immunocompetent status of humans affected with metastatic malignant melanoma.

The development of the *Monodelphis metastatic* melanoma cell lines was made possible by the introduction of animals into a UVR exposure protocol at the suckling stage. Several features of the early postnatal development of Monodelphis made this a feasible approach: a) adult Monodelphis females do not possess a pouch, so that sucklings, firmly attached to a teat, can be fully exposed from the mother's ventral surface; b) in this position, litter mates can be exposed to UVR over the dorsolateral regions of the body; c) with a maximum litter size of 13 (mean of 7), many individuals can be irradiated repeatedly for up to 18 to 19 days, before periodic detachment from the nipple normally begins; d) at this early stage of development, hair growth is rudimentary so the skin requires no shaving; and e) flexure of the head and neck shields the unopen eyes from UVR, so that the risk of induction of eye tumors is avoided.

Furthermore, the utility of the cell lines is heightened by their propensity for growth when injected into suckling young of Monodelphis when the development of immune competence is far from complete as previously suggested by Fadem and Hill, Cancer Lett, 27:233–238 (1985).

EXAMPLES

Example 1

Animals and irradiation procedures.

All animals were produced and maintained at the SFBR under unexceptional conditions similar to those used for laboratory rodents. Suckling young received their first dose of UVR from 1 to 4 days after birth. The hairless sucklings are each attached continuously to one of the dam's teats. Entire litters up to 18 days of age were exposed to UVR by placing the dam in a wire mesh-floored polypropylene or polycarbonate mouse cage, then fixing the cage above fluorescent sunlamps. The dam was free to move around the floor of the cage horizontally, but her vertical movements were inhibited by the floor of a second cage placed inside the exposure cage. In this way, the dorsal and lateral surfaces of all the pendulous litter mates received equivalent doses of UVR. Of the 37 litters exposed, 10 received non-erythemal doses of 125 $J/m^2$ of UVR every other day for up to 18 days after birth, leading to an accumulated dose of about 1.0 $kJ/m^2$. The remaining 27 litters received regimens where the number of exposures varied and the total dose increased up to levels (>4.0 $kJ/m^2$) that lead to marked erythema. Dose rates were monitored with a spectroradiometer. From the time of entry into the irradiation protocol, females with litters were housed in rooms with red fluorescent lamps to avoid photoreactivation.

All animals exposed as sucklings were shaved and examined for melanocytic lesions at or soon after weaning. On the assumption that further exposure might promote lesion growth and tumorigenesis, animals with lesions were introduced to an established juvenile (from two to five months old) and adult (from five months old) irradiation protocol (VandeBerg, et al., Arch. Dermatol. Res., 286:12–17 (1994)) of three exposures a week for up to 45 more weeks before necropsy.

Example 2

Identification of Lesions.

At the time of initial identification, melanocytic lesions were measured and recorded. Lesions were reassessed every three weeks until necropsy, at which time several animals had pigmented malignant melanoma cells present in lymph nodes.

Of the 214 animals from 37 litters that were irradiated as sucklings, 22 (10%) each possessed a single melanocytic lesion when first examined as weanlings or juveniles. At this time, lesions were usually black (rarely dark brown), round and flat with smooth margins, and 2–7 mm maximum diameter.

Eight affected animals exposed to further UVR into adulthood were necropsied and diagnosed from gross observation and histological sections as malignant melanomas with metastasis to one or more lymph nodes. Growth characteristics of the eight skin melanomas from the time of their discovery until the last adult exposure showed considerable variation.

Example 3

Establishment and Characteristics of Metastatic Melanoma Cell Lines.

Skin and lymph node biopsies from animals which had been identified as having malignant melanoma cells were removed to generate cell lines for growth in vitro. The melanocytic cell lines were established in culture at approximately 33° C., in 5% $CO_2$ from fresh, finely-minced biopsy material in "D" medium containing Iscove's Modified Dulbecco's Medium, 16% FBS, ITS (5 µg/ml insulin, 5 µg/ml transferrin, 5 ng/ml selenite), 2 mM L-glutamine, 2 mM $CaCl_2$, and 0.2% Pen-Strep (Dooley, et al., Cancer Genet. Cytogent. 71:55–66 (1993)), plus 1 nM cholera toxin and 160 nM 12-0-tetradecanoylphorbol-13-acetate (TPA). To enhance explant attachment, minimal volumes of medium were used (approximately 3–5 ml per 10 cm plate). A variety of lymph node-derived cell lines were established. The derivatives of cell line TD15L (from animal ID #B7841) have been examined in detail. Two ring-cloned isolates of the TD15L cell line (TD15L1 and TD15L2(ATCC No. CRL-11898) exhibited the following in vitro properties: The cell lines were heavily pigmented in vitro, dendritic, grew rapidly in culture, and contained a specific cytogenetic marker. Both of the sublines exhibited minimal substrate adherence. Thus, they were easily removed mechanically without the need for trypsin digestion. Furthermore, cell pellets from both these lines were black. These properties (pigmentation and dendricity) are consistent with a melanoma phenotype. The TD18L cell line (derived from animal #B9870) was also pigmented in culture but exhibited a more epithelial and adherent morphology.

Example 4

Injection of Cells into Nude Mice.

The melanocytic cell lines were tested in vivo for evidence of the tumorigenic phenotype by injecting $1 \times 10^6$ cells subcutaneously into the dorsal flanks of adult female athymic NCr-nu nude mice (NCI—Taconic Labs) to detect whether malignant tumors could be formed. Control human and murine malignant melanoma cell lines have been tested s.c. under similar conditions, and were found to be tumorigenic in NCr-nu mice (Dooley, et al., Lab. Anim. Sci., 43:48–57 (1993)). After 30, 60, 90, and 120 days, the mice were examined externally and after the last examination they were euthanized with $CO_2$ and photographed. The dorsal skin was surgically excised to determine the extent of tumor cell growth in intradermal and subcutaneous tissue before examination of internal body sites. Surprisingly, the cells did not grow into palpable tumors in the subcutis, as would be expected for human or mouse malignant melanoma cells lines. However, s.c. pigmentation was visible externally from the day of injection until necropsy. The cells clearly retained their viability, since pigmented melanoma cells could be cultured out of the mouse skin at later time. Derivatives of TD15L proliferated within the dermis of nude mice at the site of the needle tract. All intradermal lesions were densely pigmented and some skin lesions were elevated. Proliferation at this intradermal site resembled the histology of UVR-induced melanocytic nevi in Monodelphis dorsal skin. This result confirms the suspected tumorigenic potential of these *Monodelphis metastaic* melanoma cell lines.

Example 5

Injection of Cells into Monodelphis suckling young.

Monodelphis suckling young (at 1–3 weeks of age) which were injected subcutaneously (range from ca. $1.0 \times 10^4$ to $1 \times 10^6$ cells) with the melanoma cells developed invasive, pigmented, subcutaneous and cutaneous lesions, and some animals developed metastatic tumors in internal organs, especially lung. Development of primary and metastatic lesions in Monodelphis suggests that injection of the TD15L1 or TD15L2 (ATCC No. CRL-11898) cells lines (and perhaps other Monodelphis melanoma cell lines) during early postnatal development facilitates proficient allogeneic grafting in minimally inbred animals (i.e. genetically dissimilar), presumably due to underdeveloped immunocompetence and/or induced tolerance. Additional melanoma cell lines were derived from tissue biopsies from the recipient host Monodelphis (e.g., TD15M1, grown from affected lung tissue of animal ID #C4832).

While the foregoing invention has been described in some detail for purposes of clarity and understanding, it will be clear to one skilled in the art from the reading of this disclosure that various changes in form and detail can be made without departing from the true scope of the invention.

We claim:

1. Cell line TD15L2(ATCC No. CRL-11898) having metastaic, pigmented, malignant melanoma cells obtained from a lymph node of *Monodelphis domestica*.

2. A method of inducing in vivo growth of the cell line of claim 1 in Monodelphis comprising the step of injecting the Monodelphis with an amount of cells from the cell line.

3. The method according to claim 2 wherein the amount of cells injected into the Monodelphis is from $1.0 \times 10^4$ to $1 \times 10^6$ cells.

4. The method according to claim 2 wherein the Monodelphis is a *Monodelphis domestica* suckling young animal.

* * * * *